United States Patent

Gerdes et al.

[11] Patent Number: 5,534,550
[45] Date of Patent: Jul. 9, 1996

[54] 2-OXIMINO-2PHENYL-ACETAMIDES

[75] Inventors: Peter Gerdes, Aachen; Herbert Gayer, Monheim; Stefan Dutzmann, Hilden; Heinz-Wilhelm Dehne, Monheim, all of Germany

[73] Assignee: Bayer Aktiengesellschaft, Leverkusen, Germany

[21] Appl. No.: 251,807

[22] Filed: May 31, 1994

[30] Foreign Application Priority Data

Jun. 7, 1993 [DE] Germany .................. 43 18 917.2

[51] Int. Cl.$^6$ ............... A61K 31/165; C07C 233/05
[52] U.S. Cl. ............................. 514/620; 564/164
[58] Field of Search ............... 564/162, 164, 564/165, 147; 560/13, 18, 251; 558/58; 514/620

[56] References Cited

FOREIGN PATENT DOCUMENTS

| 0398692 | 11/1990 | European Pat. Off. |
| 0535928 | 4/1993 | European Pat. Off. |
| 0579124 | 1/1994 | European Pat. Off. |
| 4182461 | 6/1992 | Japan. |

OTHER PUBLICATIONS

Hayase et al. CHEM. ABSTR. 118:59429e (1993) (Abstract of JP 04,182,461).

*Primary Examiner*—Nicky Chan
*Attorney, Agent, or Firm*—Sprung Horn Kramer & Woods

[57] ABSTRACT

New 2-oximino-2-phenyl-acetamides of the formula

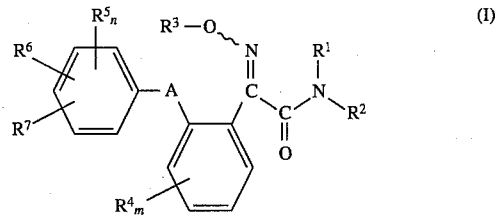

in which
$R^1, R^2, R^3, R^4, R^5, R^6, R^7$ m and n have the meanings given in the description,
a process for the preparation of the new substances, and their use as pesticides.

6 Claims, No Drawings

2-OXIMINO-2PHENYL-ACETAMIDES

The invention relates to new 2-oximino-2-phenyl-acetamides, to a process for their preparation and to their use as pesticides.

It has been disclosed that certain 2-methoximino-2-phenyl-acetates have fungicidal properties (cf. EP-OS (European Published Specification) 0,400,417). For example, methyl 2-methoximino-2-[2-(2-methylphenoxymethyl)-phenyl]-acetate can be used for combating fungi. However, the activity of this substance is not entirely satisfactory in all fields of application, in particular where the application rates are low.

New 2-oximino-2-phenyl-acetamides of the formula

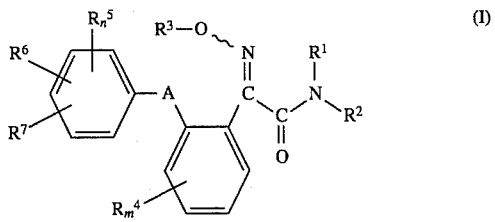

in which
$R^1$ and $R^2$ independently of one another in each case represent hydrogen, alkyl or alkoxy, $R^3$ represents hydrogen, alkyl or alkoxy, $R^4$ and $R^5$ independently of one another in each case represent halogen, cyano, nitro, formyl, carbamoyl, thiocarbamoyl, alkyl, alkoxy, alkylthio, alkylsulphinyl, alkylsulphonyl, alkenyl, alkenyloxy, halogenoalkyl, halogenoalkoxy, halogenoalkylthio, halogenoalkylsul-phinyl, halogenoalkylsulphonyl, halogenoalkenyl, halogenoalkenyloxy, N-alkylamino, dialkylamino, alkylcarbonyl, alkylcarbonyloxy, alkoxycarbonyl, alkylsulphonyloxy, hydroximinoalkyl, alkoximinoalkyl or represent in each case optionally substituted cycloalkyl, heterocyclyl, phenyl, phenoxy, benzyl, benzyloxy, phenylethyl or phenylethyloxy, m represents the numbers 0, 1, 2, 3 or 4, n represents the numbers 0, 1, 2, 3 or 4, A represents a group of the formula —CH$_2$—O—; —O—CH$_2$—; —CH$_2$—S— or —S—CH$_2$—, $R^6$ represents either hydrogen, halogen, cyano, nitro, formyl, carbamoyl, thiocarbamoyl, alkyl, alkoxy, alkylthio, alkylsulphinyl, alkylsulphonyl, alkenyl, alkenyloxy, halogenoalkyl, halogenoalkoxy, halogenoalkylthio, halogenoalkylsulphinyl, halogenoalkylsulphonyl, halogenoalkenyl, halogenoalkenyloxy, N-alkylamino, dialkylsunino, alkylcarbonyl, alkylcarbonyloxy, alkoxycarbonyl, alkylsulphonyloxy, hydroximinoalkyl, alkoximinoalkyl, or represents in each case optionally substituted cycloalkyl, heterocyclyl, phenyl, phenoxy, benzyl, benzyloxy, phenylethyl or phenylethyloxy and $R^7$ represents halogenoalkoxy or halogenoalkylthio, or $R^6$ and $R^7$ together represent an optionally substituted, bivalent alkanediyl radical which contains one or more oxygen or sulphur atoms, have now been found.

If appropriate, the compounds of the formula (I) can exist as geometric and/or optical isomers or variously composed isomer mixtures, depending on the nature of the substituents. The invention relates both to the pure isomers and to the isomer mixtures.

Furthermore, it has been found that 2-oximino-2-phenylacetamides of the formula (I) are obtained when 2-oximino-2-phenyl-acetates of the formula

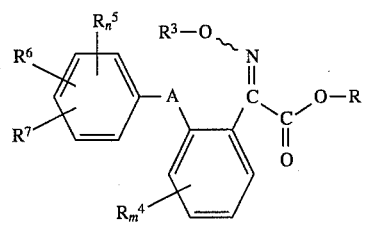

in which
$R^3$, $R^4$, $R^5$, $R^6$, $R^7$, A, m and n have the above-mentioned meanings and R represents alkyl, are reacted with ammonia or amines of the formula

in which
$R^1$ and $R^2$ have the abovementioned meanings, if appropriate in the presence of a diluent and if appropriate in the presence of an acid-binding agent.

Finally, it has been found that the new 2-oximino-2-phenyl-acetamides of the formula (I) are highly suitable for use in pest control.

Surprisingly, the 2-oximino-2-phenyl-acetamides of the formula (I) according to the invention show a considerably better activity against phytopathogenic microorganisms than methyl 2-methoximino-2-[2-(2-methyl-phenoxymethyl)-phenyl]-acetate, which is a previously known active substance having a similar constitution and the same direction of action.

Formula (I) provides a general definition of the 2-oximino-2-phenyl-acetamides according to the invention.

$R^1$ preferably represents hydrogen, straight-chain or branched alkyl having 1 to 8 carbon atoms or straight-chain or branched alkoxy having 1 to 8 carbon atoms.

$R^2$ preferably represents hydrogen, straight-chain or branched alkyl having 1 to 8 carbon atoms or straight-chain or branched alkoxy having 1 to 8 carbon atoms.

$R^3$ preferably represents hydrogen, straight-chain or branched alkyl having 1 to 8 carbon atoms or straight-chain or branched alkoxy having 1 to 8 carbon atoms.

$R^4$ preferably represents halogen, cyano, nitro, formyl, carbamoyl, thiocarbamoyl, in each case straight-chain or branched alkyl, alkoxy, alkylthio, alkylsulphinyl or alkylsulphonyl, each of which has 1 to 6 carbon atoms, in each case straight-chain or branched alkenyl or alkenyloxy, each of which has 2 to 6 carbon atoms, in each case straight-chain or branched halogenoalkyl, halogenoalkoxy, halogenoalkylthio, halogenoalkylsulphinyl or halogenoalkylsulphonyl, each of which has 1 to 6 carbon atoms and 1 to 13 identical or different halogen atoms, in each case straight-chain or branched halogenoalkenyl or halogenoalkenyloxy, each of which has 2 to 6 carbon atoms and 1 to 13 identical or different halogen atoms, in each case straight-chain or branched N-alkylamino, dialkylamino, alkylcarbonyl, alkylcarbonyloxy, alkoxycarbonyl, alkylsulphonyloxy, hydroximinoalkyl or alkoximinoalkyl, each of which has 1 to 6 carbon atoms in the individual alkyl or alkoxy moieties, furthermore represents cycloalkyl having 3 to 7 carbon atoms which is optionally monosubstituted to trisubstituted by identical or different substituents from the series comprising halogen and/or alkyl having 1 to 4 carbon atoms, further represents 3- to 7-membered heterocyclyl having 2 to 6 carbon atoms and 1 to 3 identical or different hetero atoms, such as nitrogen, oxygen and/or sulphur, and which is optionally monosubstituted to trisubstituted by identical or different substituents from the series comprising halogen and/or alkyl having 1 to 4 carbon atoms, and moreover represents phenyl, phenoxy, benzyl, benzyloxy, phenylethyl or phenylethyloxy, it being possible for each of these radicals to be monosubstituted to pentasubstituted in the phenyl moiety by identical or different substituents from the series comprising halogen, straight-chain or branched alkyl having 1 to 4 carbon atoms, straight-chain or branched halogenoalkyl having 1 to 4 carbon atoms and 1 to 9 identical or different halogen atoms, straight-chain or branched alkoxy having 1 to 4 carbon atoms and/or straight-chain or branched halogenoalkoxy having 1 to 4 carbon atoms and 1 to 9 identical or different halogen atoms.

$R^5$ preferably represents halogen, cyano, nitro, formyl, carbamoyl, thiocarbamoyl, in each case straight-chain or branched alkyl, alkoxy, alkylthio, alkylsulphinyl or alkylsulphonyl, each of which has i to 6 carbon atoms, in each case straight-chain or branched alkenyl or alkenyloxy, each of which has 2 to 6 carbon atoms, in each case straight-chain or branched halogenoalkyl, halogenoalkoxy, halogenoalkylthio, halogenoalkylsulphinyl or halogenoalkylsulphonyl, each of which has 1 to 6 carbon atoms and 1 to 13 identical or different halogen atoms, in each case straight-chain or branched halogenoalkenyl or halogenoalkenyloxy, each of which has 2 to 6 carbon atoms and 1 to 13 identical or different halogen atoms, in each case straight-chain or branched N-alkylamino, dialkylamino, alkylcarbonyl, alkylcarbonyloxy, alkoxycarbonyl, alkylsulphonyloxy, hydroximinoalkyl or alkoximinoalkyl, each of which has 1 to 6 carbon atoms in the individual alkyl or alkoxy moieties, furthermore represents cycloalkyl having 3 to 7 carbon atoms which is optionally monosubstituted to trisubstituted by identical or different substituents from the series comprising halogen and/or alkyl having 1 to 4 carbon atoms, further represents 3- to 7-membered heterocyclyl having 2 to 6 carbon atoms and 1 to 3 identical or different hetero atoms, such as nitrogen, oxygen and/or sulphur, and which is optionally monosubstituted to trisubstituted by identical or different substituents from the series comprising halogen and/or alkyl having 1 to 4 carbon atoms, and moreover represents phenyl, phenoxy, benzyl, benzyloxy, phenylethyl or phenylethyloxy, it being possible for each of these radicals to be monosubstituted to pentasubstituted in the phenyl moiety by identical or different substituents from the series comprising halogen, straight-chain or branched alkyl having 1 to 4 carbon atoms, straight-chain or branched halogenoalkyl having 1 to 4 carbon atoms and 1 to 9 identical or different halogen atoms, straight-chain or branched alkoxy having 1 to 4 carbon atoms, straight-chain or branched halogenoalkoxy having 1 to 4 carbon atoms and 1 to 9 identical or different halogen atoms.

m preferably represents the numbers 0, 1, 2, 3 or 4, it being possible for $R^4$ to represent identical or different radicals if m represents 2, 3 or 4.

n preferably represents the numbers 0, 1, 2, 3 or 4, it being possible for $R^5$ to represent identical or different radicals if n represents 2, 3 or 4.

A preferably represents a group of the formula —CH$_2$—O—, —O—CH$_2$—, —CH$_2$—S— or —S—CH$_2$—.

$R^6$ preferably represents hydrogen, halogen, cyano, nitro, formyl, carbamoyl, thiocarbamoyl, in each case straight-chain or branched alkyl, alkoxy, alkylthio, alkylsulphinyl or alkylsulphonyl, each of which has 1 to 6 carbon atoms, in each case straight-chain or branched alkenyl or alkenyloxy, each of which has 2 to 6 carbon atoms, in each case straight-chain or branched halogenoalkyl, halogenoalkoxy, halogenoalkylthio, halogenoalkylsulphinyl or halogenoalkylsulphonyl, each of which has 1 to 6 carbon atoms and 1 to 13 identical or different halogen atoms, in each case straight-chain or branched halogenoalkenyl or halogenoalkenyloxy, each of which has 2 to 6 carbon atoms and 1 to 13 identical or different halogen atoms, in each case straight-chain or branched N-alkylamino, dialkylamino, alkylcarbonyl, alkylcarbonyloxy, alkoxycarbonyl, alkylsulphonyloxy, hydroximinoalkyl or alkoximinoalkyl, each of which has 1 to 6 carbon atoms in the individual alkyl or alkoxy moieties, furthermore represents cycloalkyl having 3 to 7 carbon atoms which is optionally monosubstituted to trisubstituted by identical or different substituents from the series comprising halogen and/or alkyl having 1 to 4 carbon atoms, further represents 3- to 7-membered heterocyclyl having 2 to 6 carbon atoms and 1 to 3 identical or different hetero atoms, such as nitrogen, oxygen and/or sulphur, and which is optionally monosubstituted to trisubstituted by identical or different substituents from the series comprising halogen and/or alkyl having 1 to 4 carbon atoms, and moreover represents phenyl, phenoxy, benzyl, benzyloxy, phenylethyl or phenylethyloxy, it being possible for each of these radicals to be monosubstituted to pentasubstituted in the phenyl moiety by identical or different substituents from the series comprising halogen, straight-chain or branched alkyl having 1 to 4 carbon atoms, straight-chain or branched halogenoalkyl having 1 to 4 carbon atoms and 1 to 9 identical or different halogen atoms, straight-chain or branched alkoxy having 1 to 4 carbon atoms and/or straight-chain or branched halogenoalkoxy having 1 to 4 carbon atoms and 1 to 9 identical or different halogen atoms.

$R^7$ preferably in each case represents straight-chain or branched halogenoalkoxy or halogenoalkylthio, each of which has 1 to 8 carbon atoms and 1 to 17 identical or different halogen atoms—in particular fluorine, chlorine, bromine and/or iodine.

$R^6$ and $R^7$ together furthermore also preferably represent a bivalent alkanediyl radical having 1 to 5 carbon atoms which contains 1 to 3 oxygen and/or sulphur atoms and which is optionally monosubstituted to hexasubstituted by identical or different substituents from the series comprising halogen, straight-chain or branched halogenoalkyl having 1 to 6 carbon atoms and 1 to 13 identical or different halogen atoms—in particular fluorine, chlorine, bromine and/or iodine.

$R^1$ particularly preferably represents hydrogen, straight-chain or branched alkyl having 1 to 6 carbon atoms or straight-chain or branched alkoxy having 1 to 6 carbon atoms.

$R^2$ particularly preferably represents hydrogen, straight-chain or branched alkyl having 1 to 6 carbon atoms or straight-chain or branched alkoxy having 1 to 6 carbon atoms.

$R^3$ particularly preferably represents hydrogen, straight-chain or branched alkyl having 1 to 6 carbon atoms or straight-chain or branched alkoxy having 1 to 6 carbon atoms.

$R^4$ particularly preferably represents fluorine, chlorine, bromine, cyano, nitro, formyl, carbamoyl, thiocarbamoyl, in each case straight-chain or branched alkyl, alkoxy, alkylthio, alkylsulphinyl or alkylsulphonyl, each of which has 1 to 4 carbon atoms, in each case straight-chain or branched alkenyl or alkenyloxy, each of which has 2 to 4 carbon atoms, in each case straight-chain or branched halogenoalkyl, halogenoalkoxy, halogenoalkylthio, halogenoalkylsulphinyl or halogenoalkylsulphonyl, each of which has 1 to 4 carbon atoms and 1 to 9 fluorine, chlorine and/or bromine atoms, in each case straight-chain or branched halogenoalkenyl or halogenoalkenyloxy, each of which has 2 to 4 carbon atoms and 1 to 9 fluorine, chlorine and/or bromine atoms, in each case straight-chain or branched N-alkylamino, dialkylamino, alkylcarbonyl, alkylcarbonyloxy, alkoxycarbonyl, alkylsulphonyloxy, hydroximinoalkyl or alkoximinoalkyl, each of which has 1 to 4 carbon atoms in the individual alkyl or alkoxy moieties, furthermore represents cycloalkyl having 3 to 6 carbon atoms which is optionally monosubstituted to trisubstituted by identical or different substituents from the series comprising fluorine, chlorine, methyl and/or ethyl, furthermore represents 3- to 7-membered heterocyclyl which has 2 to 5 carbon atoms and 1 to 3 identical or different hetero atoms, such as nitrogen, oxygen and/or sulphur, and which is optionally monosubstituted to trisubstituted by identical or different substituents from the series comprising fluorine, chlorine, methyl and/or ethyl, and moreover represents phenyl, phenoxy, benzyl, benzyloxy, phenylethyl or phenylethyloxy, it being possible for each of these radicals to be monosubstituted to pentasubstituted in the phenyl moiety by identical or different substituents from the series comprising fluorine, chlorine, bromine, straight-chain or branched alkyl having 1 to 3 carbon atoms, straight-chain or branched halogenoalkyl having 1 to 3 carbon atoms and 1 to 7 fluorine, chlorine and/or bromine atoms, straight-chain or branched alkoxy having 1 to 3 carbon atoms and/or straight-chain or branched halogenoalkoxy having 1 to 3 carbon atoms and 1 to 7 fluorine, chlorine, and/or bromine atoms.

$R^5$ particularly preferably represents fluorine, chlorine, bromine, cyano, nitro, formyl, carbamoyl, thiocarbamoyl, in each case straight-chain or branched alkyl, alkoxy, alkylthio, alkylsulphinyl or alkylsulphonyl, each of which has 1 to 4 carbon atoms, in each case straight-chain or branched alkenyl or alkenyloxy, each of which has 2 to 4 carbon atoms, in each case straight-chain or branched halogenoalkyl, halogenoalkoxy, halogenoalkylthio, halogenoalkylsulphinyl or halogenoalkylsulphonyl, each of which has 1 to 4 carbon atoms and 1 to 9 fluorine, chlorine and/or bromine atoms, in each case straight-chain or branched halogenoalkenyl or halogenoalkenyloxy, each of which has 2 to 4 carbon atoms and 1 to 9 fluorine, chlorine and/or bromine atoms, in each case straight-chain or branched N-alkylamino, dialkylamino, alkylcarbonyl, alkylcarbonyloxy, alkoxycarbonyl, alkylsulphonyloxy, hydroximinoalkyl or alkoximinoalkyl, each of which has 1 to 4 carbon atoms in the individual alkyl or alkoxy moieties, furthermore represents cycloalkyl having 3 to 6 carbon atoms which is optionally monosubstituted to trisubstituted by identical or different substituents from the series comprising fluorine, chlorine, methyl and/or ethyl, furthermore represents 3- to 7-membered heterocyclyl which has 2 to 5 carbon atoms and 1 to 3 identical or different hetero atoms, such as nitrogen, oxygen and/or sulphur, and which is optionally monosubstituted to trisubstituted by identical or different substituents from the series comprising fluorine, chlorine, methyl and/or ethyl, and moreover represents phenyl, phenoxy, benzyl, benzyloxy, phenylethyl or phenylethyloxy, it being possible for each of these radicals to be monosubstituted to pentasubstituted in the phenyl moiety by identical or different substituents from the series comprising fluorine, chlorine, bromine, straight-chain or branched alkyl having 1 to 3 carbon atoms, straight-chain or branched halogenoalkyl having 1 to 3 carbon atoms and 1 to 7 fluorine, chlorine and/or bromine atoms, straight-chain or branched alkoxy having 1 to 3 carbon atoms and/or straight-chain or branched halogenoalkoxy having 1 to 3 carbon atoms and 1 to 7 fluorine, chlorine and/or bromine atoms. particularly preferably represents the numbers 0, 1, 2 or 3, it being possible for $R^4$ to represent identical or different radicals if m represents 2 or 3.

n particularly preferably represents the numbers 0, 1, 2 or 3, it being possible for $R^5$ to represent identical or different radicals if n represents 2 or 3.

A particularly preferably represents a group of the formula —CH$_2$—O—, —O—CH$_2$—, —CH$_2$—S— or —S—CH$_2$—.

$R^6$ particularly preferably represents hydrogen, fluorine, chlorine, bromine, cyano, nitro, formyl, carbamoyl, thiocarbamoyl, in each case straight-chain or branched alkyl, alkoxy, alkylthio, alkylsulphinyl or alkylsulphonyl, each of which has 1 to 4 carbon atoms, in each case straight-chain or branched alkenyl or alkenyloxy, each of which has 2 to 4 carbon atoms, in each case straight-chain or branched halogenoalkyl, halogenoalkoxy, halogenoalkylthio, halogenoalkylsulphinyl or halogenoalkylsulphonyl, each of which has 1 to 4 carbon atoms and 1 to 9 fluorine, chlorine and/or bromine atoms, in each case straight-chain or branched halogenoalkenyl or halogenoalkenyloxy, each of which has 2 to 4 carbon atoms and 1 to 9 fluorine, chlorine and/or bromine atoms, in each case straight-chain or branched N-alkylamino, dialkylamino, alkylcarbonyl, alkylcarbonyloxy, alkoxycarbonyl, alkylsulphonyloxy, hydroximinoalkyl or alkoximinoalkyl, each of which has 1 to 4 carbon atoms in the individual alkyl or alkoxy moieties, furthermore represents cycloalkyl having 3 to 6 carbon atoms which is optionally monosubstituted to trisubstituted by identical or different substituents from the series comprising fluorine, chlorine, methyl and/or ethyl, furthermore represents 3- to 7-membered heterocyclyl which has 2 to 5 carbon atoms and 1 to 3 identical or different hetero atoms, such as nitrogen, oxygen and/or sulphur, and which is optionally monosubstituted to trisubstituted by identical or different substituents from the series comprising fluorine, chlorine, methyl and/or ethyl, and moreover represents phenyl, phenoxy, benzyl, benzyloxy, phenylethyl or phenylethyloxy, it being possible for each of these radicals to be monosubstituted to pentasubstituted in the phenyl moiety by identical or different substituents from the series comprising fluorine, chlorine, bromine, straight-chain or branched alkyl having 1 to 3 carbon atoms, straight-chain or branched halogenoalkyl having 1 to 3 carbon atoms and 1 to 7 fluorine, chlorine and/or bromine atoms, straight-chain or branched alkoxy having 1 to 3 carbon atoms and/or straight-chain or branched halogenoalkoxy having 1 to 3 carbon atoms and 1 to 7 fluorine, chlorine and/or bromine atoms.

$R^7$ particularly preferably represents in each case straight-chain or branched halogenoalkoxy or halogenoalkylthio, each of which has 1 to 4 carbon atoms and 1 to 9 fluorine, chlorine and/or bromine atoms.

$R^6$ and $R^7$ together furthermore also particularly preferably represent a bivalent alkanediyl radical having 1 to 4 carbon atoms which contains 1 or 2 oxygen and/or sulphur atoms and which is optionally monosubstituted to hexasubstituted by identical or different substituents from the series comprising fluorine, chlorine, bromine, straight-chain or branched alkyl having 1 to 4 carbon atoms and/or straight-chain or branched halogenoalkyl having 1 to 4 carbon atoms and 1 to 9 fluorine, chlorine and/or bromine atoms.

$R^1$ very particularly preferably represents hydrogen, straight-chain or branched alkyl having 1 to 4 carbon atoms or straight-chain or branched alkoxy having 1 to 4 carbon atoms.

$R^2$ very particularly preferably represents hydrogen, straight-chain or branched alkyl having 1 to 4 carbon atoms or straight-chain or branched alkoxy having 1 to 4 carbon atoms.

$R^3$ very particularly preferably represents hydrogen, straight-chain or branched alkyl having 1 to 4 carbon atoms or straight-chain or branched alkoxy having 1 to 4 carbon atoms.

$R^4$ very particularly preferably represents fluorine, chlorine, bromine, cyano, nitro, formyl, carbamoyl, thiocarbamoyl, methyl, ethyl, n- or i-propyl, n-, i-, s- or t-butyl, methoxy, ethoxy, n- or i-propoxy, n-, i-, s- or t-butoxy, methylthio, ethylthio, methylsulphinyl, methylsulphonyl, allyl, butenyl, allyloxy, butenyloxy, trifluoromethyl, trifluoromethoxy, difluoromethoxy, trifluoromethylthio, difluorochloromethylthio, trifluoromethylsulphinyl, trifluoromethylsulphonyl, dimethylamino, diethylamino, acetyl, acetoxy, methylsulphonyloxy, ethylsulphonyloxy, methoxycarbonyl, ethoxycarbonyl, hydroximinomethyl, hydroximinoethyl, methoximinomethyl, methoximinoethyl, ethoximinomethyl, ethoximinoethyl, cyclopropyl, cyclopentyl, cyclohexyl, 1-pyrrolidinyl, 1-piperidinyl, 1-perhydroazepinyl, 4-morpholinyl, or represents phenyl, phenoxy, benzyl, benzyloxy, phenylethyl or phenylethyloxy, it being possible for each of the six last-mentioned radicals to be monosubstituted to trisubstituted in the phenyl moiety by identical or different substituents from the series comprising fluorine, chlorine, bromine, methyl, ethyl, methoxy, ethoxy, trifluoromethyl and/or trifluoromethoxy.

$R^5$ very particularly preferably represents fluorine, chlorine, bromine, cyano, nitro, formyl, carbamoyl, thiocarbamoyl, methyl, ethyl, n- or i-propyl, n-, i-, s- or t-butyl, methoxy, ethoxy, n- or i-propoxy, n-, i-, s- or t-butoxy, methylthio, ethylthio, methylsulphinyl, methylsulphonyl, allyl, butenyl, allyloxy, butenyloxy, trifluoromethyl, trifluoromethoxy, difluoromethoxy, trifluoromethylthio, difluorochloromethylthio, trifluoromethylsulphinyl, trifluoromethylsulphonyl, dimethylamino, diethylamino, acetyl, acetoxy, methylsulphonyloxy, ethylsulphonyloxy, methoxycarbonyl, ethoxycarbonyl, hydroximinomethyl, hydroximinoethyl, methoximinomethyl, methoximinoethyl, ethoximinomethyl, ethoximinoethyl, cyclopropyl, cyclopentyl, cyclohexyl, 1-pyrrolidinyl, 1-piperidinyl, 1-perhydroazepinyl, 4 -morpholinyl, or represents phenyl, phenoxy, benzyl, benzyloxy, phenylethyl or phenylethyloxy, it being possible for each of the six last-mentioned radicals to be monosubstituted to trisubstituted in the phenyl moiety by identical or different substituents from the series comprising fluorine, chlorine, bromine, methyl, ethyl, methoxy, ethoxy, trifluoromethyl and/or trifluoromethoxy.

m very particularly preferably represents the numbers 0, 1 or 2, it being possible for $R^4$ to represent identical or different radicals if m represents 2.

n very particularly preferably represents the numbers 0, 1 or 2, it being possible for $R^5$ to represent identical or different radicals if n represents 2.

A very particularly preferably represents a group of the formula —$CH_2$—O—, —O—$CH_2$—, —$CH_2$—S— or —S—$CH_2$—.

$R^6$ very particularly preferably represents hydrogen, fluorine, chlorine, bromine, cyano, nitro, formyl, carbamoyl, thiocarbamoyl, methyl, ethyl, n- or i-propyl, n-, i -, s- or t-butyl, methoxy, ethoxy, n- or i-propoxy, n-, i-, s- or t-butoxy, methylthio, ethylthio, methylsulphinyl, methylsulphonyl, allyl, butenyl, allyloxy, butenyloxy, trifluoroinethyl, trifluoroinethoxy, difluoromethoxy, trifluoroinethylthio, difluorochloroinethylthio, trifluoroinethylsulphinyl, trifluoroinethylsulphonyl, diinethylamino, diethyl amino, acetyl, acetoxy, methylsulphonyloxy, ethylsulphonyloxy, methoxycarbonyl, ethoxycarbonyl, hydroxiininoinethyl, hydroxiininoethyl, methoximinomethyl, methoximinoethyl, ethoximinomethyl, ethoximinoethyl, cyclopropyl, cyclopentyl, cyclohexyl, 1-pyrrolidinyl, 1-piperidinyl, 1 -perhydroazepinyl, 4-morpholinyl, or represents phenyl, phenoxy, benzyl, benzyloxy, phenylethyl or phenylethyloxy, it being possible for each of the six last-mentioned radicals to be monosubstituted to trisubstituted in the phenyl moiety by identical or different substituents from the series comprising fluorine, chlorine, bromine, methyl, ethyl, methoxy, ethoxy, trifluoromethyl and/or trifluoromethoxy.

$R^7$ very particularly preferably represents straight-chain or branched halogenoalkoxy having 1 to 3 carbon atoms and 1 to 7 fluorine, chlorine and/or bromine atoms, or represents straight-chain or branched halogenoalkylthio having 1 to 3 carbon atoms and 1 to 7 fluorine, chlorine and/or bromine atoms.

$R^6$ and $R^7$ together furthermore very particularly preferably represent a bivalent alkanediyl radical having 1 to 3 carbon atoms which contains 1 to 2 oxygen or sulphur atoms and which is optionally monosubstituted to tetrasubstituted by identical or different substituents from the series comprising fluorine, chlorine, bromine, methyl, ethyl and/or trifluoromethyl.

The following 2-oximino-2-phenyl-acetamides of the formula (I) may be mentioned individually in addition to the compounds mentioned in the preparation examples:

TABLE 1

(I)

| $-NR^1R^2$ | $R^3$ | $R_m^4$ | A | $R_n^5$ | $R^6$ | $R_7$ |
|---|---|---|---|---|---|---|
| $-NH-CH_3$ | $CH_3$ | H | $-O-CH_2-$ | H | 2-$CH_3$ | 4-$OCF_3$ |
| $-NH-CH_3$ | $CH_3$ | H | $-O-CH_2-$ | H | 2-$CH_3$ | 4-O—$CF_2$—$CF_2Cl$ |
| $-NH-CH_3$ | $CH_3$ | H | $-O-CH_2-$ | H | 2-$CH_3$ | 4-O—$CF_2$—$CHF_2$ |
| $-NH_2$ | $CH_3$ | H | $-O-CH_2-$ | H | 2-Cl | 4-$OCF_3$ |
| $-NH_2$ | $CH_3$ | H | $-O-CH_2-$ | H | H | 2-O—$CHF_2$ |
| $-NH_2$ | $CH_3$ | H | $-O-CH_2-$ | H | 2-$CH_3$ | 4-$OCF_3$ |

TABLE 1-continued

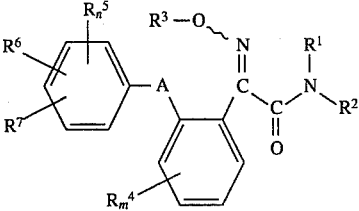

| -NR¹R² | R³ | R$_m^4$ | A | R$_n^5$ | R⁶ | R₇ |
|---|---|---|---|---|---|---|
| -NH₂ | CH₃ | H | -O-CH₂- | H | 2-CH₃ | 4-O-CF₂-CF₂Cl |
| -NH₂ | CH₃ | H | -O-CH₂- | H | 2-CH₃ | 4-O-CF₂-CHF₂ |
| -NH-CH₃ | CH₃ | H | -O-CH₂- | H | | 3,4-O-CF₂-CF₂-O- |
| -NH-CH₃ | CH₃ | H | -O-CH₂- | H | | 3,4-CF₂-O-CF₂-O- |
| -NH-CH₃ | CH₃ | H | -O-CH₂- | H | | 3,4-CF₂-O-CF₂- |
| -NH-CH₃ | CH₃ | H | -O-CH₂- | H | | 3,4-O-CF₂-CH₂-O- |
| -NH-CH₃ | CH₃ | H | -O-CH₂- | H | | 3,4-O-CF₂-CFCl-O- |
| -NH-CH₃ | CH₃ | H | -O-CH₂- | H | | 3,4-O-CF₂-CHF-O- |
| -NH-CH₃ | CH₃ | H | -O-CH₂- | H | | 3,4-CF₂-CHF-O- |
| -NH-CH₃ | CH₃ | H | -O-CH₂- | H | | 3,4-O-CF₂-O- |
| -NH₂ | CH₃ | H | -O-CH₂- | H | | 3,4-O-CF₂-CF₂-O- |
| -NH₂ | CH₃ | H | -O-CH₂- | H | | 3,4-CF₂-O-CF₂-O- |
| -NH₂ | CH₃ | H | -O-CH₂- | H | | 3,4-CF₂-O-CF₂- |
| -NH₂ | CH₃ | H | -O-CH₂- | H | | 3,4-O-CF₂-CH₂-O- |
| -NH₂ | CH₃ | H | -O-CH₂- | H | | 3,4-O-CF₂-CFCl-O- |
| -NH₂ | CH₃ | H | -O-CH₂- | H | | 3,4-O-CF₂-CHF-O- |
| -NH₂ | CH₃ | H | -O-CH₂- | H | | 3,4-CF₂-CHF-O- |
| -NH₂ | CH₃ | H | -O-CH₂- | H | | 3,4-O-CF₂-O- |

If, for example, methyl 2-[2-(2-chloro-4-trifluoromethoxy-phenoxymethyl)]-phenyl-2-methoximino-acetate and methylamine are used as starting substances, the course of the process according to the invention can be illustrated by the following equation:

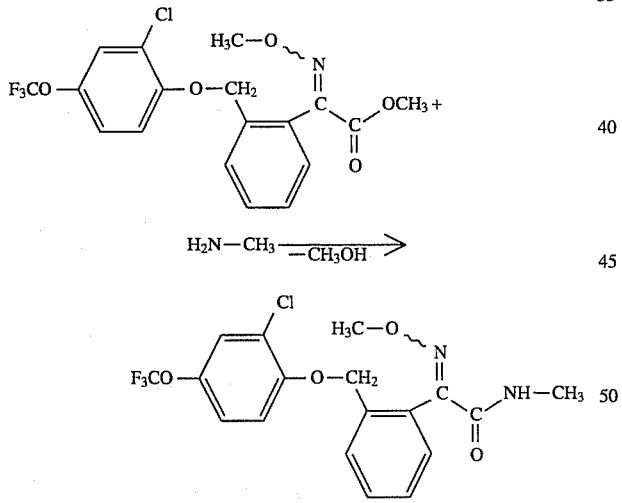

Formula (II) provides a general definition of the 2-oximino-2-phenyl-acetates required as starting compounds for carrying out the process according to the invention. In this formula (II), R³, R⁴, R⁵, R⁶, R⁷, A, m and n preferably represent those radicals and indices which have already been mentioned in connection with the description of the compounds of the formula (I) according to the invention as being preferred for these substituents and these indices. R preferably represents straightchain or branched alkyl having 1 to 4 carbon atoms, in particular methyl or ethyl.

2-Oximino-2-phenyl-acetates of the formula (II) are known or can be prepared by processes known in principle (cf., for example, EP-OS (European Published Specification) 0,253,213; EP-OS (European Published Specification) 0,398,692; EP-OS (European Published Specification) 0,400,417 and EP-OS (European Published Specification) 0,477,631). For example, 2-oximino-2-phenyl-acetates of the formula (II) are obtained by reacting (thio)phenols of the formula

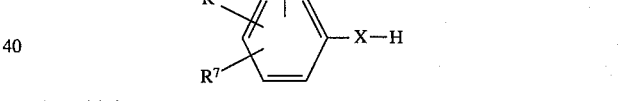

in which

R⁵, R⁶, R⁷ and n have the abovementioned meaning and X represents oxygen or sulphur, with 2-(2-halogenomethylphenyl)-2-methoximinoacetates of the formula

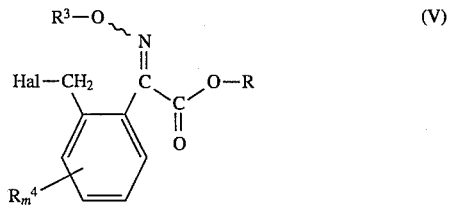

in which

R, R³, R⁴ and m have the abovementioned meaning and X represents halogen, at temperatures between −20° C. and +80° C., if appropriate in the presence of a diluent, such as, for example, N,N-dimethylformamide, and, if appropriate, in the presence of an acid-binding agent, such as, for example, sodium hydride.

(Thio)phenols of the formula (IV) are generally known compounds of organic chemistry or can be obtained in analogy to known processes (cf. DE-OS (German Published Specification) 3,836,175).

2-(2-Halogenomethylphenyl)-2-methoximinoacetates of the formula (V) are also known or can be obtained in analogy to known processes (cf. EP-OS (European Published Specification) 0,254,426).

Formula (III) provides a General definition of ammonia or the amines which are furthermore required as starting substances for carrying out the process according to the invention. In this formula (III), $R^1$ and $R^2$ preferably represent those radicals which have already been mentioned in connection with the description of the compounds of the formula (I) according to the invention as being preferred for these substituents.

The amines of the formula (III) and ammonia are generally known compounds of organic chemistry.

Suitable diluents for carrying out the process according to the invention are inert organic solvents. The following can preferably be used: aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl ether or ethylene glycol diethyl ether; nitriles, such as acetonitrile, propionitrile or benzonitrile; amides, such as N,N-dimethylformamide, N,N-dimethylacetamide, N-methylformanilide, N-methylpyrrolidone or hexamethylphosphoric triamide, or sulphoxides, such as dimethyl sulphoxide.

The process according to the invention is preferably carried out in the presence of an acid-binding agent. Suitable acid-binding agents are all customary inorganic or organic bases. The following can preferably be used: the hydrides, hydroxides, amides, alcoholates, acetates, carbonates or hydrogen carbonates of alkaline earth metals or alkali metals, and also ammonium compounds, such as, for example, sodium hydride, sodium amide, sodium methylate, sodium ethylate, potassium tert.-butylate, sodium hydroxide, potassium hydroxide, ammonium hydroxide, sodium acetate, potassium acetate, calcium acetate, ammonium acetate, sodium carbonate, potassium carbonate, potassium hydrogen carbonate, sodium hydrogen carbonate or ammonium carbonate, and also tertiary amines, such as trimethylamine, triethylamine, tributylamine, N,N-dimethylaniline, pyridine, N-methylpiperidine, N,N-dimethylaminopyridine, diazahicyclooctane (DABCO), diazabicyclononene (DBN) or diazahicycloundecene (DBU). It is also possible to employ the amine of the formula (III), which is used as reactant, in a suitable excess to act simultaneously as acid-binding agent.

When carrying out the process according to the invention, the reaction temperatures can be varied within a substantial range. In general, the process is carried out at temperatures between −30° C. and +150° C., preferably at temperatures between −20° C. and +120° C.

The process according to the invention is conventionally carried out under atmospheric pressure. However, it is also possible to carry out the process under increased or reduced pressure.

To carry out the process according to the invention, 1.0 to 3.0 mol, preferably 1.0 to 1.5 mol, of amine of the formula (III) and, if appropriate, 0.1 to 3.0 mol, preferably 0.5 to 1.5 mol, of acid-binding agent are generally employed per mole of 2-oximino-2-phenylacetate of the formula (II). In a particular embodiment, it is also possible to prepare the 2-oximino- 2-phenyl-acetates of the formula (II), which are used as starting materials, in a preceding reaction in the reaction vessel and then to further react them without isolation directly in a so-called "one-pot reaction" by the process according to the invention. The reaction is carried out and the reaction products are worked up and isolated in each case in the customary manner.

The end products of the formula (I) are purified with the aid of customary processes, for example by column chromatography or by recrystallization. They are characterized with the aid of the melting point or, in the case of compounds which do not crystallize, with the aid of the refractive index or proton nuclear resonance spectroscopy ($^1$H NMR).

The active compounds according to the invention have a powerful activity against pests and can be employed in practice for combating undesired microorganisms. The active compounds are suitable for use as plant protection agents, in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal and bacterial diseases which come under the genetic names listed above may be mentioned as examples, but not by way of limitation:

Pythium species, such as, for example, *Pythium ultimum;*

Phytophthora species, such as, for example, *Phytophthora infestans;*

Pseudoperonospora species, such as, for example, *Pseudoperonospora humuli* or *Pseudoperonospora cubensis;*

Plasmopara species, such as, for example, *Plasmopara viticola;*

Peronospora species, such as, for example, *Peronospora pisi* or *Peronospora brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *Pyrenophora graminea* (conidia form: Drechslera, syn: Helminthosporium);

Cochliobolus species, such as, for example, *Cochliobolus sativus* (conidia form: Drechslera, syn: Helminthosporitun);

Uromyces species, such as, for example, *Uromyces appendiculatus;*

Puccinia species, such as, for example, *Puccinia recondita;*

Tilletia such as, for species, example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such for as, example, *Fusarium culmorum;*

Botrytis species, such for as, example, *Botrytis cinerea;*

Septoria species, such as, for example, *Septoria nodorum;*

Leptosphaeria species, such as, for example, *Leptosphaeria nodorum;*

Cercospora species, such as, for example, *Cercospora canescens;*

Alternaria species, such as, for example, *Alternaria brassicae* and

Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

The active compounds according to the invention can be employed particularly successfully for combating diseases in fruit and vegetable growing, such as, for example, against the causative organism of tomato blight (*Phytophthora infestans*) or against the causative organism of downy mildew of grapevines (*Plasmopara viticola*) or against the causative organism of Sclerotinia disease of beans (*Sclerotinia sclerotiorum*) or against the causative organism of apple scab (*Venturia inaequalis*) or against the causative organism of powdery mildew of cucumbers (*Sphaerotheca fuliginea*) or against the causative organism of apple mildew (*Podosphaera leucotricha*) or against the causative organism of powdery mildew of grapevines (*Uncinula necator*), or for combating cereal diseases, such as, for example, against the causative organism of foot rot in wheat (*Pseudocercosporella herpotrichoides*) or against the causative organism of powdery mildew of cereals (*Erysiphe graminis*) or against the causative organism of net blotch of barley (*Pyrenophora teres*) or against the causative organism of spot blotch of barley or wheat (*Cochliobolus sativus*) or against the causative organism of glume blotch of wheat (*Septoria nodorum*) or against Fusarium species or for combating rice diseases, such as, for example, against the causative organism of rice blast disease (*Pyricularia oryzae*). In addition, the active compounds according to the invention have a good in-vitro activity.

Depending on their particular physical and/or chemical properties, the active compounds can be converted into the customary formulations, such as solutions, emulsions, suspensions, powders, foams, pastes, granules, aerosols, very fine capsules in polymeric substances and in coating compositions for seed, as well as ULV cold-mist and warm-mist formulations. These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colourants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc. The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, as well as in mixtures with fertilizers and growth regulators.

The active compounds can be used as such or in the form of their formulations or the use forms prepared therefrom, such as ready-to-use solutions, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated.

In the treatment of parts of plants, the active compound concentrations in the use forms can be varied within a substantial range: they are, in general, between 1 and 0.0001% by weight, preferably between 0.5 and 0.001% by weight.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

The preparation and the use of the substances according to the invention can be seen from the examples which follow.

Preparation examples

Example 1

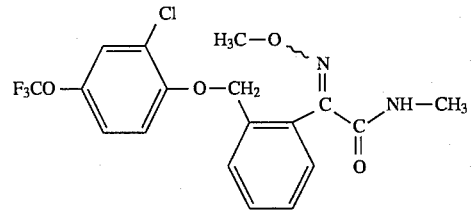

0.6 g (0.02 mol) of sodium hydride (80 per cent) is added at 0° C. with stirring to a solution of 4.2 g (0.02 mol) of 2-chloro-4-trifluoromethoxyphenol and 8.1 g (0.02 mol) of methyl 2-(2-bromomethylphenyl)-2-methoximino-acetate in 50 ml of N,N-dimethylformamide, and the batch is subsequently allowed to come slowly to room temperature and stirred for 4 hours at this temperature. For working-up, 50 ml of water are added and the mixture is extracted using ethyl acetate. The organic phase is dried, concentrated under reduced pressure, and the residue is taken up in 50 ml of methanol. 6.2 ml (0.062 mol) of methylamine solution (30 per cent strength in water) is added to the resulting solution, the mixture is subsequently stirred for 16 hours at room temperature, and the solvent is then removed under reduced pressure. The residue is purified by chromatography on silica gel (eluent: ethyl acetate/hexane).

2.5 g (48% of theory) of N-methyl-2-[2- (2-chloro-4-trfluoromethoxy-phenoxymethyl)-phenyl] -2-methoximinoacetamide are obtained as an oil.

$^1$H NMR (CDCl$_3$/tetramethylsilane): d=2.88 ( d, 3H); 3.93 (s, 3H); 5.06 (s,-2H); 6.75 (s, 1H-); 7.2 (m, 7H ppm The following 2-oximino-2-phenyl-acetamides of the formula (I) are obtained in a corresponding manner and following the general preparation instructions

TABLE 2

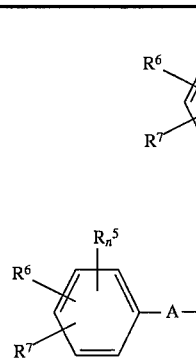

(I)

| Ex. No. | 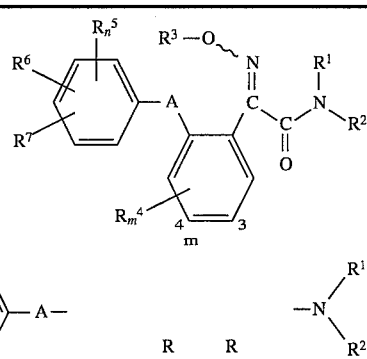 | R | R | $-N\begin{smallmatrix}R^1\\R^2\end{smallmatrix}$ | Physical properties |
|---|---|---|---|---|---|
| 2 | 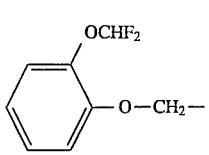 | H | CH$_3$ | —NH—CH$_3$ | $^1$H NMR*$^)$ 2.87; 3.92; 5.03; 63–76 |
| 3 | 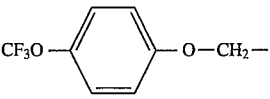 | H | CH$_3$ | —NHCH$_3$ | $^1$H-NMR*$^)$ 2,88(d); 3,92(s); 4.94(s) |
| 4 | 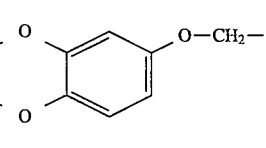 | H | CH$_3$ | —NHCH$_3$ | $^1$H-NMR*$^)$ 2,90(d); 3,94(s); 4,92(s) |
| 5 | 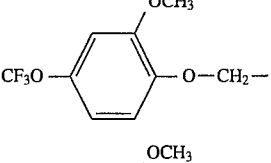 | H | CH$_3$ | —NHCH$_3$ | $^1$H-NMR*$^)$ 2,89(d); 3,95(s); 5,02(s) |
| 6 | 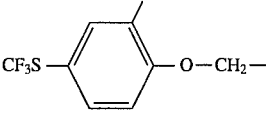 | H | CH$_3$ | —NHCH$_3$ | MS 428, 397, 368, 340, 205 |
| 7 | 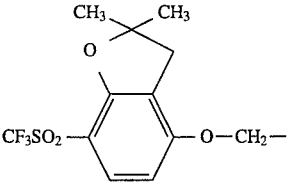 | H | CH$_3$ | —NHCH$_3$ | MS M$^+$-31(469), 396, 398, 295, 205 |

TABLE 2-continued

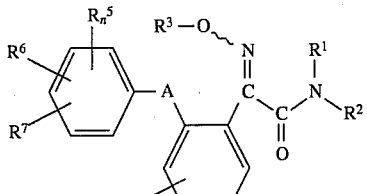

| Ex. No. | R⁶ Rₙ⁵ A— R⁷ | R | R | -N R¹ R² | Physical properties |
|---|---|---|---|---|---|
| 8 | H₃C—⬡(CF₃S)(H₃C)—O—CH₂— | H | CH₃ | —NHCH₃ | ¹H-NMR*⁾ 2,90(d); 3,94(s); 4,93(s) |

*⁾The ¹H NMR spectra were recorded in deuterochloroform (CDCl₃) or hexadeuterodimethyl sulphoxide (DMSO-d₆) with tetramethylsilane (TMS) as the internal standard. The data given is the chemical shift as δ value in ppm.

Use examples

In the use examples which follow, the compounds given below was employed as comparison substance:

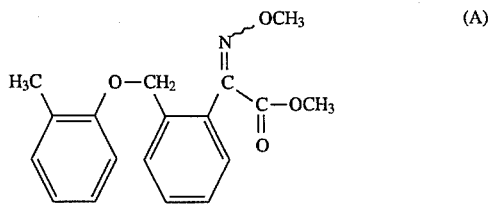

Methyl 2-methoximino-2-[2-(2-methyl-phenoxymethyl)phenyl]-acetate (disclosed in EP-OS (European Published Specification) 0,400,417)

Example A
Phytophthora Test (tomato)/protective
Solvent: 4.7 parts by weight of acetone
Emulsifier: 0.3 part by weight of alkyl-aryl polyglycol ether To produce a suitable preparation of active compound, one part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of *Phytophthora infestans*.

The plants remain in an incubation cabin at 20° C. and 100% relative atmospheric humidity.

The test is evaluated 3 days after inoculation.

In this test, a degree of effectiveness of over 80% is shown by the substance given in Example 1 according to the invention at an active compound concentration of 10 ppm in the spray mixture, while comparison substance (A) only shows a degree of effectiveness of 71%.

Example B
Plasmopara test (grapevine)/protective
Solvent: 4.7 parts by weight of acetone
Emulsifier: 0.3 part by weight of alkyl-aryl polyglycol ether To produce a suitable preparation of active compound, one part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of *Plasmopara viticola* and the plants then remain in a humid chamber at 20° C. to 22° C. and 100% relative atmospheric humidity for one day. The plants are subsequently placed in a greenhouse at 21° C. and 90% atmospheric humidity for 5 days. The plants are then moistened and placed into a humid chamber for one day.

The test is evaluated 6 days after inoculation.

In this test, a degree of effectiveness of over 80% is shown by the substance given in Example 1 according to the invention at an active compound concentration of 2.5 ppm in the spray mixture, while comparison substance (A) shows a degree of effectiveness of 40%.

Example C
Sclerotinia test (dwarf bean)/protective
Solvent: 4.7 parts by weight of acetone
Emulsifier: 0.3 part by weight of alkyl-aryl polyglycol ether To produce a suitable preparation of active compound, one part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, two small agar pieces covered with *Sclerotinia sclerotiorum* are placed onto each leaf. The inoculated plants are placed in a darkened, humid chamber at 20° C.

The size of the lesions is evaluated 3 days after inoculation.

In this test, a degree of effectiveness of over 90% is shown by the substance given in Example 1 according to the invention at an active compound concentration of 100 ppm in the spray mixture, while comparison substance (A) shows a degree of effectiveness of 74%.

Example D

Pseudocercosporella herpotrichoides test (wheat)/protective

Solvent: 12.4 parts by weight of dimethylformamide
Emulsifier: 0.6 part by weight of alkyl-aryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the given amount of the preparation of active compound. After the spray coating has dried on, the plants are inoculated at the stem base with spores of *pseudocercosporella herpotrichoides*.

The plants are placed in a greenhouse at a temperature of approximately 10° C. and a relative atmospheric humidity of approximately 80%.

The test is evaluated 21 days after inoculation.

In this test, a degree of effectiveness of 100% is shown by the substance given in Example 1 according to the invention at an active compound concentration of 400 g/ha, while comparison substance (A) is ineffective.

We claim:

1. A 2-oximinoacetamide of the formula

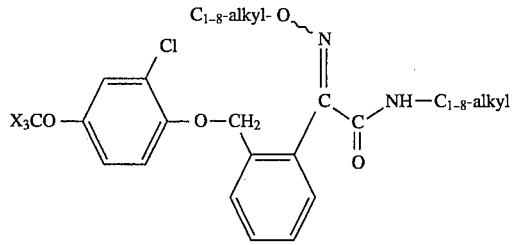

in which

X is halogen.

2. A compound according to claim 1, wherein $C_{1-8}$-alkyl is methyl.

3. A compound according to claim 1, wherein such compound is N-methyl-2-[2-(2-chloro-4-trifluoromethoxyphenoxymethyl)-phenyl]-2-methoximino-acetamide of the formula

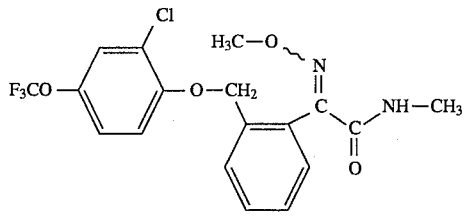

4. A fungicidal composition comprising a fungicidally effective amount of a compound according to claim 1 and a diluent.

5. A method of combatting fungi which comprises applying to such fungi or to a fungicidal habitat a fungicidally effective amount of a 2-oximino-2-phenyl-acetamide according to claim 1.

6. A method of combatting fungi which comprises applying to such fungi or to a fungicidal habitat a fungicidally effective amount of a 2-oximino-2-phenyl-acetamide according to claim 3.

* * * * *

UNITED STATES PATENT AND TRADEMARK OFFICE
CERTIFICATE OF CORRECTION

PATENT NO. : 5,534,550
DATED      : July 9, 1996
INVENTOR(S): Gerdes, et al.

It is certified that error appears in the above-indentified patent and that said Letters Patent is hereby corrected as shown below:

Title Page & Col 1   Title [54]:  After " 2-OXIMINO-2 "
line 1               insert -- - --

Signed and Sealed this

Eighteenth Day of March, 1997

Attest:

BRUCE LEHMAN

*Attesting Officer*   Commissioner of Patents and Trademarks